(12) United States Patent
Swoish et al.

(10) Patent No.: US 10,132,256 B2
(45) Date of Patent: Nov. 20, 2018

(54) PARTICULATE FILTER DEVICE MONITORING SYSTEM FOR AN ENGINE

(71) Applicant: GM Global Technology Operations LLC, Detroit, MI (US)

(72) Inventors: Christopher C. Swoish, Lapeer, MI (US); Christopher Whitt, Howell, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 865 days.

(21) Appl. No.: 13/891,875

(22) Filed: May 10, 2013

(65) Prior Publication Data

US 2014/0331654 A1 Nov. 13, 2014

(51) Int. Cl.
| | |
|---|---|
| F02D 41/02 | (2006.01) |
| G01N 15/06 | (2006.01) |
| F01N 9/00 | (2006.01) |
| F02D 41/08 | (2006.01) |
| F02D 41/14 | (2006.01) |
| G01N 15/08 | (2006.01) |
| F01N 3/10 | (2006.01) |
| F01N 3/20 | (2006.01) |
| F01N 3/022 | (2006.01) |
| F01N 13/00 | (2010.01) |

(52) U.S. Cl.
CPC ......... *F02D 41/029* (2013.01); *F01N 9/002* (2013.01); *F01N 9/005* (2013.01); *G01N 15/06* (2013.01); *F01N 3/0222* (2013.01); *F01N 3/106* (2013.01); *F01N 3/2066* (2013.01); *F01N 13/009* (2014.06); *F01N 13/0093* (2014.06); *F01N 2330/06* (2013.01); *F01N 2550/04* (2013.01); *F01N 2560/06* (2013.01); *F01N 2560/14* (2013.01); *F01N 2900/1606* (2013.01); *F02D 41/08* (2013.01); *F02D 41/1445* (2013.01); *F02D 2200/0812* (2013.01); *G01N 2015/084* (2013.01); *Y02T 10/47* (2013.01)

(58) Field of Classification Search
CPC ........ F02D 41/029; F02D 41/08; G01N 15/06
See application file for complete search history.

(56) References Cited

U.S. PATENT DOCUMENTS

| | | | |
|---|---|---|---|
| 2002/0196153 A1* | 12/2002 | Kinugawa | ............... F01N 9/002 340/606 |
| 2005/0016137 A1* | 1/2005 | Hamahata | ............... F01N 9/002 55/283 |
| 2005/0022520 A1 | 2/2005 | Shirakawa et al. | |
| 2007/0056274 A1* | 3/2007 | Wills | ............................. 60/297 |

(Continued)

OTHER PUBLICATIONS

Office Action dated Jan. 18, 2016 in corresponding CN Patent Application No. 201410194301.2.

*Primary Examiner* — Mark Laurenzi
*Assistant Examiner* — Jason Sheppard
(74) *Attorney, Agent, or Firm* — Cantor Colburn LLP

(57) ABSTRACT

A particulate filter device monitoring system for an engine includes a regeneration mode trigger module configured to set a regeneration request based on soot accumulation in the particulate filter device, a regeneration control module configured to control regeneration of the particulate filter device, and a soot out model module including a soot out model configured to calculate changes in soot out rate during prolonged engine idling periods.

10 Claims, 4 Drawing Sheets

(56) References Cited

U.S. PATENT DOCUMENTS

| | | | | |
|---|---|---|---|---|
| 2009/0044514 A1* | 2/2009 | Brahma | ............... | F01N 9/002 60/274 |
| 2009/0288398 A1* | 11/2009 | Perfetto | ............... | F02D 41/029 60/287 |
| 2010/0126145 A1* | 5/2010 | He et al. | ............... | 60/286 |
| 2010/0313629 A1* | 12/2010 | Singh | ............... | F01N 3/023 73/23.31 |
| 2011/0153179 A1* | 6/2011 | Guglielmone | ............... | F01N 3/023 701/102 |
| 2011/0320171 A1* | 12/2011 | Okayama | ............... | B01D 46/0086 702/183 |
| 2012/0116645 A1* | 5/2012 | Hamahata | ............... | F01N 3/0256 701/102 |

* cited by examiner

PARTICULATE FILTER DEVICE MONITORING SYSTEM FOR AN ENGINE

FIELD OF THE INVENTION

The subject invention relates to engine emission monitoring systems and, more particularly, to a particulate filter device monitoring system for an engine.

BACKGROUND

Exhaust gas emitted from an internal combustion engine, particularly a diesel engine, is a heterogeneous mixture that contains gaseous emissions such as, but not limited to, carbon monoxide ("CO"), unburned hydrocarbons ("HC") and oxides of nitrogen ("$NO_x$") as well as condensed phase materials (liquids and solids) that constitute diesel particulate matter ("PM"). Catalyst compositions, typically disposed on catalyst supports or substrates, are provided in an engine exhaust system as part of an aftertreatment system to convert certain, or all of these exhaust constituents into non-regulated exhaust gas components.

One type of exhaust treatment technology for reducing emissions is a diesel particulate filter ("DPF"). The DPF is designed to remove diesel particulate matter or soot from exhaust gas of a diesel engine. The diesel particulate matter removed from the exhaust is entrapped by, and entrained in, the DPF. When accumulated soot reaches a predetermined level the DPF is either replaced or regenerated. Replacement or regeneration ensures that soot removal continues at desired parameters.

Many engines include a controller having a soot out model that predicts soot accumulation in the DPF. The soot out monitor employs various engine operating parameters to predict soot accumulation levels in the DPF. The operating parameters include duration and number of accelerations, duration of operating at constant RPM above idle, and idle time. Inaccurate soot accumulation predictions could lead to premature replacement or cleaning of a DPF, or operating conditions in which soot is not removed at desired levels. Accordingly, it is desirable to provide a soot out model that more accurately reflects soot accumulation during all operating conditions.

SUMMARY OF THE INVENTION

In accordance with an exemplary embodiment, a particulate filter device monitoring system for an engine includes a regeneration mode trigger module configured to set a regeneration request based on soot accumulation in the particulate filter device, a regeneration control module configured to control regeneration of the particulate filter device, and a soot out model module including a soot out model configured to calculate changes in soot out rate during prolonged engine idling periods.

In accordance with another exemplary embodiment, an internal combustion engine includes an engine including an exhaust conduit, a particulate filter device fluidically connected to the exhaust gas conduit, and a particulate filter device monitoring system having a control module configured to monitor soot accumulation in the particulate filter device and implement a regeneration mode. The control module includes a regeneration mode trigger configured to set a regeneration request based on soot accumulation in the particulate filter device, a regeneration control module configured to control regeneration of the particulate filter device, and a soot out model module including a soot out model configured to calculate changes in soot out rate during prolonged engine idling periods.

In accordance with yet another exemplary embodiment, a method of monitoring particulate accumulation in a particulate filter device is discussed. The method includes calculating an amount of particulate in a particulate filter device employing a soot out model, adjusting the soot out model during periods of prolonged idle, and regenerating the particulate filter device when the amount of particulate reaches a particulate threshold value.

The above features and advantages and other features and advantages of the invention are readily apparent from the following detailed description of the invention when taken in connection with the accompanying drawings.

BRIEF DESCRIPTION OF THE DRAWINGS

Other features, advantages and details appear, by way of example only, in the following detailed description of embodiments, the detailed description referring to the drawings in which.

DESCRIPTION OF THE EMBODIMENTS

Figure 1:
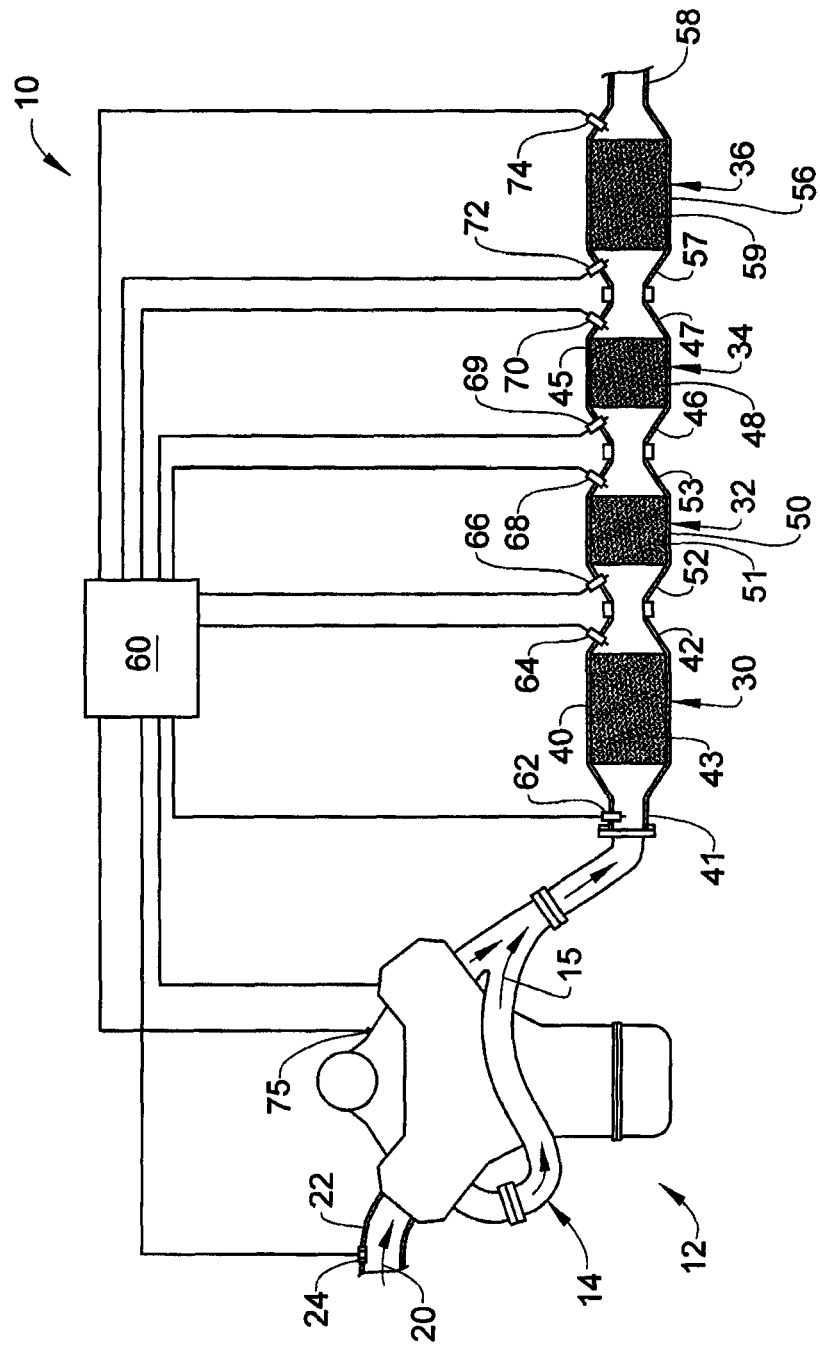
FIG. 1 is a schematic diagram of a particulate filter device monitoring system including a control module in accordance with exemplary embodiments.

The following description is merely exemplary in nature and is not intended to limit the present disclosure, its application or uses. It should be understood that throughout the drawings, corresponding reference numerals indicate like or corresponding parts and features. As used herein, the term "module" refers to an application specific integrated circuit (ASIC), an electronic circuit, a processor (shared, dedicated, or group) and memory that executes one or more software or firmware programs, and/or a combinational logic circuit. When implemented in software, a module can be embodied in memory as a non-transitory machine-readable storage medium readable by a processing circuit and storing instructions for execution by the processing circuit for performing a method.

Referring now to FIG. 1, an exemplary embodiment is directed to a particulate filter device monitoring system 10 for an internal combustion ("IC") engine 12. An exhaust gas conduit 14, which may comprise several segments, transports exhaust gas 15 from the engine 12 to various aftertreatment devices. More specifically, engine 12 is configured to receive an intake air 20 from an air intake passage 22. The intake air passage 22 includes an intake mass airflow sensor 24 for determining the intake air mass of the engine 12. In one embodiment, the intake mass airflow sensor 24 may be either a vane meter or a hot wire type intake mass airflow sensor; however, it is to be understood that other types of sensors may be used as well. Intake air 20 mixes with fuel (not shown) to form a combustible mixture. The combustible mixture is compressed to combustion pressure in a combustion chamber of engine 12 producing work, i.e., engine output and exhaust gases 15. Exhaust gases 15 pass from the engine 12 to various aftertreatment devices of the particulate filter device monitoring system 10.

In the exemplary embodiment as illustrated, aftertreatment devices of the particulate filter device monitoring system 10 include a first oxidation catalyst ("OC") device 30, a selective catalytic reduction ("SCR") device 32, a second OC device 34, and a particulate filter ("PF") device 36. As can be appreciated, the particulate filter device monitoring system 10 of the present disclosure may include various combinations of one or more of the aftertreatment devices shown in FIG. 1, and/or other aftertreatment devices (e.g., lean $NO_x$ traps), and is not limited to the present example.

First OC device 30 includes a casing 40 having an inlet 41 in fluid communication with exhaust gas conduit 14 and an outlet 42. Casing 40 may surround a flow-through metal or ceramic monolith substrate 43. Similarly, second OC device 34 includes a casing 45 having an inlet 46 and an outlet 47. Casing 45 may surround a flow-through metal or ceramic monolith substrate 48. Flow-through metal or ceramic monolith substrates 43 and 48 can include an oxidation catalyst compound disposed thereon. The oxidation catalyst compound may be applied as a wash coat and may contain platinum group metals such as platinum ("Pt"), palladium ("Pd"), rhodium ("Rh") or other suitable oxidizing catalysts, or combinations thereof. The OC devices 30 and 34 are useful in treating unburned gaseous HC and CO, which are oxidized to form carbon dioxide and water.

SCR device 32 may be disposed downstream of first OC device 30 and upstream of second OC device 34. In a manner similar to the OC devices 30 and 34, SCR device 32 includes a shell or canister 50 that houses a flow-through ceramic or metal monolith substrate 51. Canister 50 includes an inlet 52 in fluid communication with outlet 42 of first OC device 30 and an outlet 53 in fluid communication with second OC device 34. Substrate 51 may include an SCR catalyst composition applied thereto. The SCR catalyst composition may contain a zeolite and one or more base metal components such as iron ("Fe"), cobalt ("Co"), copper ("Cu") or vanadium ("V") which can operate efficiently to convert $NO_x$ constituents in the exhaust gas 15 in the presence of a reductant such as ammonia.

PF device 36 may be disposed downstream of SCR device 32 and the second OC device 34. PF device 36 operates to filter exhaust gas 15 of carbon and other particulates (soot). PF device 36 includes a housing 56 having an inlet 57 fluidically coupled to outlet 47 of second OC device 34 and an outlet 58 that may discharge to ambient. Housing 56 may surround a ceramic wall flow monolith filter 59. Ceramic wall flow monolith filter 59 may have a plurality of longitudinally extending passages (not separately labeled) that are defined by longitudinally extending walls (also not separately labeled). The passages include a subset of inlet passages that have an open inlet end and a closed outlet end, and a subset of outlet passages that have a closed inlet end and an open outlet end. Exhaust gas 15 entering the filter 59 through the inlet ends of the inlet passages is forced to migrate through adjacent longitudinally extending walls to the outlet passages. It is through this wall flow mechanism that the exhaust gas 15 is filtered of carbon and other particulates. The filtered particulates are deposited on the longitudinally extending walls of the inlet passages and, over time, will have the effect of increasing exhaust gas backpressure experienced by the engine 12. It is appreciated that the ceramic wall flow monolith filter 59 is merely exemplary in nature and that the PF device 36 may include other filter devices such as wound or packed fiber filters, open cell foams, sintered metal fibers, etc. The increase in exhaust gas backpressure caused by the accumulation of particulate matter in the monolith filter 59 typically requires that the PF device 36 is periodically replaced, cleaned, or regenerated. Regeneration involves the oxidation or burning of the accumulated carbon and other particulates in what is typically a high temperature environment (>600° C.).

A control module 60 is operably connected to and monitors the engine 12 and the particulate filter device monitoring system 10 through a number of sensors. FIG. 1 illustrates the control module 60 in communication with the engine 12, intake mass airflow sensor 24, first and second temperature sensors 62 and 64 for determining the temperature profile of the first OC device 30, third and fourth temperature sensors 66 and 68 for determining the temperature profile of the SCR device 32, fifth and sixth temperature sensors 69 and 70 for determining the temperature profile of the second OC device 34, and seventh and eighth temperature sensors 72 and 74 for determining the temperature profile of the PF device 36 and a tachometer 75 for determining engine speed and engine accelerations.

The control module 60 determines, in part, an amount of particulate matter or soot accumulation in PF device 36. Soot accumulation in PF device 36 leads to an increase in exhaust gas backpressure on engine 12. The increase in exhaust gas backpressure caused by the accumulation of soot in the monolith filter 59 typically requires that the PF device 36 is periodically replaced, cleaned, or regenerated. Regeneration involves the oxidation or burning of the accumulated carbon and other particulates in what is typically a high temperature environment (>600° C.).

In accordance with one exemplary aspect of the invention, control module 60 includes logic that monitors operating parameters of engine 12 including temperatures, accelerations, and exhaust mass flow. Exhaust mass flow is based on the intake air mass of the engine 12, which is measured by the intake air mass airflow sensor 24 as well as a fuel mass flow of the engine 12. Specifically, the exhaust mass flow is calculated by adding the intake air mass of the engine 12 and the fuel mass flow of the engine 12. Based on the monitored parameters, control module 60 calculates soot accumulation in PF device 36.

Figure 2:
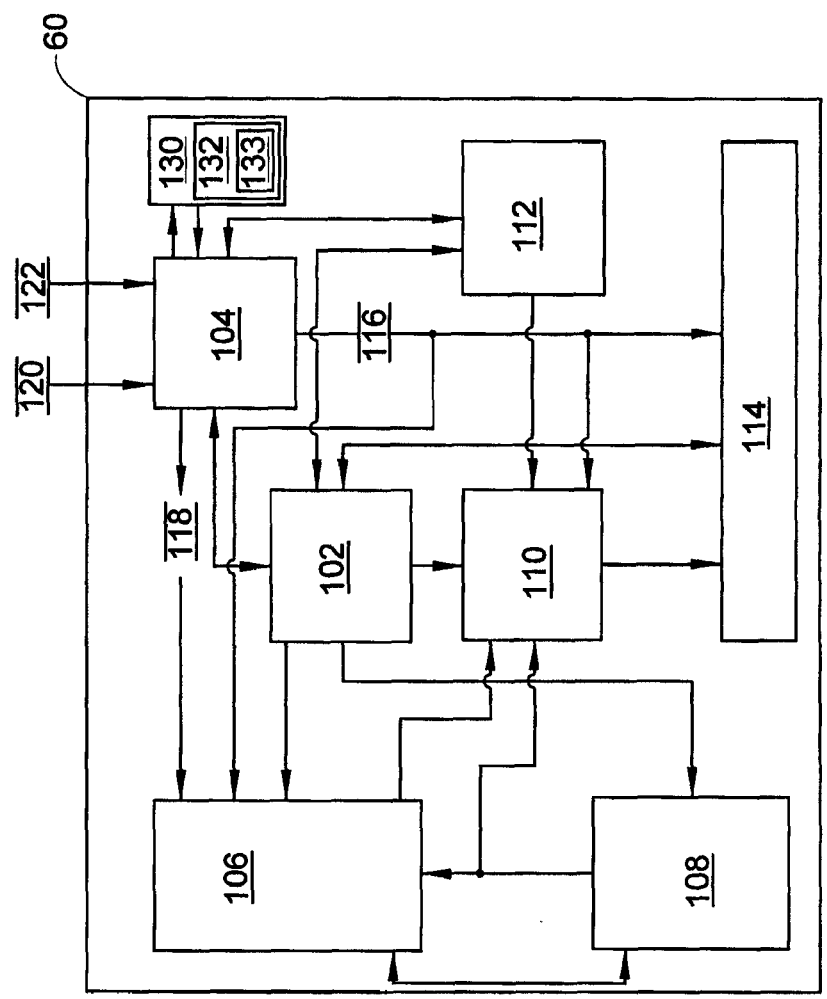
FIG. 2 is a dataflow diagram of the control module shown in FIG. 1 in accordance with exemplary embodiments.

FIG. 2 is an illustration of a dataflow diagram that illustrates various elements that may be embedded within the control module 60. Various embodiments of the particulate filter device monitoring system 10 of FIG. 1, according to the present disclosure, may include any number of sub-modules embedded within the control module 60. As can be appreciated, the sub-modules shown in FIG. 2 may be combined or further partitioned as well. Inputs to control module 60 may be sensed from the particulate filter device monitoring system 10, received from other control modules (not shown), or determined by other sub-modules or modules. In the embodiment as shown in FIG. 2, control module 60 includes a memory 102, a regeneration control module 104, a regeneration mode trigger module 106, a soot accumulation counter module 108, an idle time counter module 110, an interrupt module 112 and a fuel injection control module 114. Control module 60 also includes a regeneration mode switch 116 and a soot accumulation register 118.

In one embodiment, the memory 102 of the control module 60 stores a number of configurable limits, maps, and variables that are used to calculate soot accumulation and control regeneration of PF device 36 of FIG. 1. Each of the modules 104-114 interfaces with the memory 102 to retrieve and update stored values as needed. For example, the memory 102 can provide values to the regeneration control module 104 for supporting determination of a soot load in soot accumulation register 118 and thresholds for activating regeneration mode trigger 106 based on vehicle operating conditions 120 and exhaust conditions 122.

The regeneration control module 104 may apply algorithms known in the art to determine when to set a regeneration mode switch 116 to activate regeneration mode trigger module 106 when an amount of particulate in PF device 36 of FIG. 1 reaches a particular threshold value. For example, the regeneration mode switch 116 may be set when the soot load in soot accumulation register 118 exceeds a threshold defined in the memory 102. Regeneration of the PF device 36 of FIG. 1 can be based, on or limited, according to a soot out model module 130 connected to regeneration control module 104. Regeneration control module 104 compares vehicle operating conditions 120 and exhaust conditions 122 with a soot out model 132 provided in soot out model module 130 to calculate soot accumulation in PF device 36 and determine when a regeneration cycle is indicated. The vehicle operating conditions 120 and the exhaust conditions 122 can be provided by sensors or other modules. For example, the seventh and eighth temperature sensors 72, 74 (shown in FIG. 1) send electrical signals to the control module 60, of FIG. 1, to indicate a temperature profile of the PF device 36 of FIG. 1. Factors such as engine speed, exhaust temperature, time elapsed since a last regeneration, distance traveled since a last regeneration, fuel consumed since a last regeneration, and a modeled soot level can also be used to determine when the regeneration mode switch 116 should be set.

In accordance with an exemplary embodiment, soot out model 132 includes an extended idle correction factor 133 that adjusts for changes in soot out rate occurring during prolonged idle periods. As sown in FIG. 3, particulate, or soot output, increases at a steady substantially linear rate for a first period 150 of a prolonged or extended period. At a threshold 160, soot output increases at a substantially exponential rate for a second portion 170 of the extended period. Extended idle correction factor 133 includes a multiplier that enables soot out model 132 to adjust for soot out rate error that may occur during idle, particularly the increasing soot expulsion during second portion 170. Extended idle correction factor 133 enables soot out model 132 to change soot output rate as idle time increases to more accurately predict soot accumulation in PF device 36 of FIG. 1 to reduce occurrences of premature regeneration or replacement.

Figure 3:
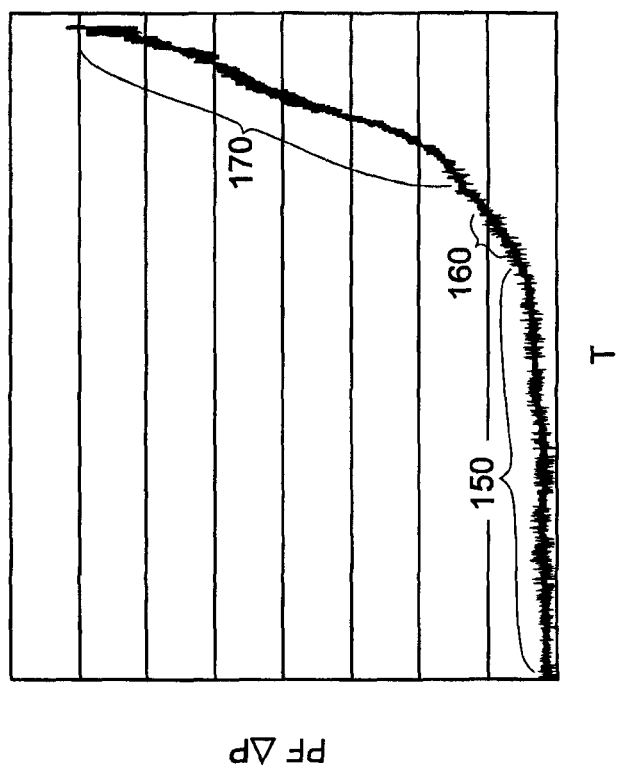
FIG. 3 is a graph depicting particulate discharge during an extended idle period.
Figure 4:
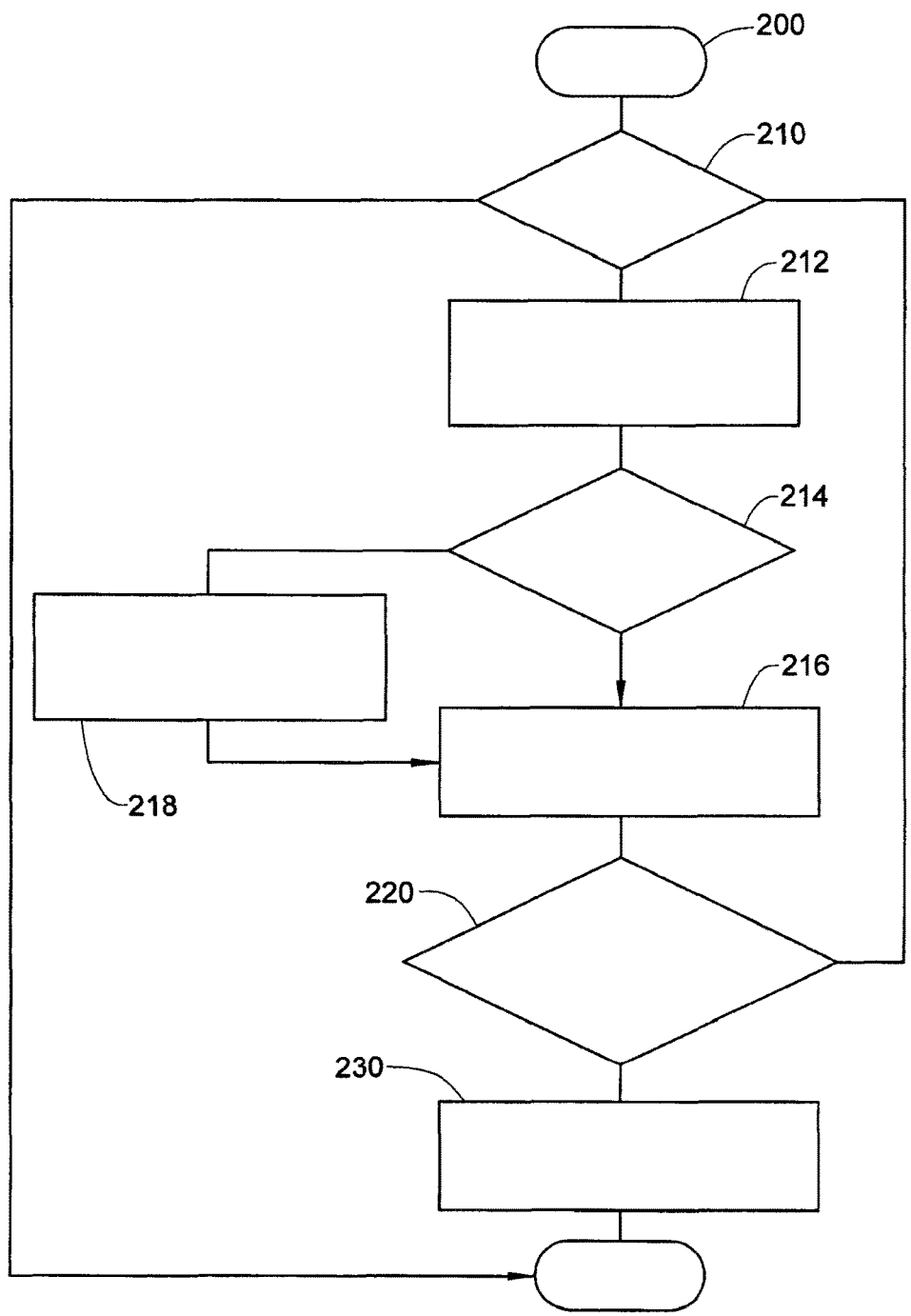
FIG. 4 is a flowchart illustrating a method of monitoring a particulate filter device in accordance with an exemplary embodiment.

Turning to FIG. 4, and with continued reference to FIGS. 1, 2 and 3, a flowchart illustrates a method for monitoring particulate or soot accumulation in PF device 36, of FIG. 1, that can be performed by the control module 60 of FIG. 1 in accordance with the present disclosure. As can be appreciated in light of the disclosure, the order of operation within the method is not limited to the sequential execution as illustrated in FIG. 4, but may be performed in one or more varying orders as applicable and in accordance with the present disclosure. It should also be appreciated that in various embodiments, the method can be scheduled to run based on predetermined events, and/or run continually during operation of the engine 12 of FIG. 1.

In one example, the method may begin at block 200. At block 210, control module 60, of FIG. 1, determines whether engine 12, of FIG. 1, is operating. If engine 12, of FIG. 1, is operating, at block 212 control module 60 signals soot model module 130 to calculate soot accumulation in PF device 36 of FIG. 1. Control module 60 determines, in block 214, if engine 12, of FIG. 1, is in an extended idle period. If not, soot out model module 130 stores calculated soot accumulation value in soot accumulation register 118, of FIG. 2, as indicated in block 216. If engine 12 is in an extended idle period, soot out model module 130 applies extended idle correction factor 133 to soot out model 132 in block 218 and corrected soot accumulation is stored in soot accumulation register 118 of FIG. 2. Control module 60 determines in block 220 whether the accumulated soot value is above a predetermined threshold value. If the accumulated soot value is below the threshold value, control module 60 continues to calculate soot accumulation. If, however, the accumulated soot value is above the threshold value, control module 60 signals regeneration mode switch 116 to set regeneration mode trigger module 106 to initiate activation of regeneration control module 104, as indicated in block 230. Regeneration control module 104 begins a regeneration process to refresh a ceramic wall flow monolith filter 59.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the application.

What is claimed is:

1. A particulate filter device monitoring system for an engine comprising:
   a particulate filter device including at least one sensor;
   a regeneration mode trigger module configured to set a regeneration request based on soot accumulation in the particulate filter device based on signals received from the at least one sensor;
   a regeneration control module configured to control regeneration of the particulate filter device; and
   a soot out model module including a soot out model configured to calculate changes in a soot out rate during an extended engine idle period.

2. The particulate filter device monitoring system according to claim 1, wherein the soot out model module includes an extended idle correction factor that corrects for soot out error during the extended engine idle period.

3. The particulate filter device monitoring system according to claim 2, wherein the extended idle correction factor comprises a multiplier configured to adjust the soot out model to account for a substantially exponential change in the soot out rate during the extended engine idle period.

4. The particulate filter device monitoring system according to claim 1, further comprising: a soot accumulation register operably connected with the regeneration control module, the soot accumulation register being configured to store an amount of soot in a particulate filter calculated by the soot out model module.

5. The particulate filter device monitoring system according to claim 4, further comprising: a regeneration mode switch configured to signal the regeneration mode trigger module to initiate a regeneration mode based on the amount of soot in the particulate filter calculated by the soot out model module.

6. An internal combustion engine comprising: an engine including an exhaust gas conduit;
   a particulate filter device fluidically connected to the exhaust gas conduit; and
   a particulate filter device monitoring system having a control module configured to monitor a soot accumulation in the particulate filter device and implement a regeneration mode, the control module comprising:

a regeneration mode trigger module configured to set a regeneration request based on the soot accumulation in the particulate filter device;

a regeneration control module configured to control regeneration of the particulate filter device; and a soot out model module including a soot out model configured to calculate changes in a soot out rate during an extended engine idle period.

7. The internal combustion engine according to claim 6, wherein the soot out model module includes an extended idle correction factor that corrects for soot out error during the extended engine idle period.

8. The internal combustion engine according to claim 7, wherein the extended idle correction factor comprises a multiplier configured to adjust the soot out model to account for a substantially exponential change in the soot out rate during the extended engine idle period.

9. The internal combustion engine according to claim 6, further comprising: a soot accumulation register operably connected with the regeneration control module, the soot accumulation register being configured to store an amount of soot in a particulate filter calculated by the soot out model module.

10. The internal combustion engine according to claim 9, further comprising: a regeneration mode switch configured to signal the regeneration mode trigger module to initiate a regeneration mode based on the amount of soot in the particulate filter calculated by the soot out model module.

* * * * *